US009953733B2

(12) United States Patent
Le et al.

(10) Patent No.: US 9,953,733 B2
(45) Date of Patent: Apr. 24, 2018

(54) RADIOISOTOPE CONCENTRATOR

(71) Applicant: Cyclopharm Limited, Lucas Heights, New South Wales (AU)

(72) Inventors: Van So Le, Gymea (AU); Nabil Marcos, Cronulla (AU); James McBrayer, Killarney (AU)

(73) Assignee: Cyclopharm Limited, Lucas Heights (AU)

( * ) Notice: Subject to any disclaimer, the term of this patent is extended or adjusted under 35 U.S.C. 154(b) by 430 days.

(21) Appl. No.: 14/438,575

(22) PCT Filed: Oct. 25, 2013

(86) PCT No.: PCT/AU2013/001234
§ 371 (c)(1),
(2) Date: Apr. 24, 2015

(87) PCT Pub. No.: WO2014/063198
PCT Pub. Date: May 1, 2014

(65) Prior Publication Data
US 2015/0279490 A1 Oct. 1, 2015

(30) Foreign Application Priority Data

Oct. 25, 2012 (AU) ................................ 2012904683

(51) Int. Cl.
*G21G 1/06* (2006.01)
*G21G 1/00* (2006.01)
*A61K 51/12* (2006.01)

(52) U.S. Cl.
CPC ....... *G21G 1/0005* (2013.01); *A61K 51/1286* (2013.01)

(58) Field of Classification Search
CPC .......... G21G 1/00; G21G 1/0005; G21G 1/04; A61K 51/1286
See application file for complete search history.

(56) References Cited

U.S. PATENT DOCUMENTS 5,275,802 A 1/1994 Knapp, Jr. et al.
5,729,821 A 3/1998 Knapp et al.
(Continued)

FOREIGN PATENT DOCUMENTS

WO 2008/130881 A1 10/2008
WO 2012/060923 A1 5/2012
WO 2015/039170 A1 3/2015

OTHER PUBLICATIONS

International Search Report for PCT/AU2013/001234, dated Feb. 3, 2014, 6 pages.

*Primary Examiner* — Marshall P O'Connor
(74) *Attorney, Agent, or Firm* — Seed IP Law Group LLP

(57) ABSTRACT

A system using a radioisotope concentrator device comprising a body having at least one injection port and at least one valve being configurable between a first open configuration for allowing fluid communication between the at least one injection port and the concentrator column and a second open configuration to prevent fluid communication between the at least one injection port and the concentrator column in use, the system further comprising an injection device comprising an eluent for eluting through the concentrator column via the at least one injection port when the at least one valve of the radioisotope concentrator device is in a selected open configuration in use.

18 Claims, 6 Drawing Sheets

(56) References Cited

U.S. PATENT DOCUMENTS 6,157,036 A * 12/2000 Whiting ............... G21G 1/0005
250/430
2010/0320136 A1 12/2010 Lin et al.

* cited by examiner

RADIOISOTOPE CONCENTRATOR

BACKGROUND

Technical Field

The present disclosure relates to radioisotope purification and concentration, and in particular to a radioisotope concentrator device for use with a radioisotope source, a system, and a process for capturing at least one radioisotope from a radioisotope solution obtained from a radioisotope source.

The disclosure has been developed primarily for use in conjunction with a radioisotope source provided in the form of a radioisotope generator configured for generating the radioisotope solution or a vial containing the radioisotope solution source and will be described hereinafter with reference to this application. However, it will be appreciated that the disclosure is not limited to this particular field of use.

Description of the Related Art

Technetium-99m ($^{99m}Tc$) is a metastable isotope of technetium. This means it has at least two modes of decay with two different half-lives. The decay mode with the shorter half-life is approximately 6 hours and decays via gamma ray emission (with an energy of 140 keV) to its ground state which in turn decays via pure beta emission with a half-life of $2.13 \times 10^5$ years to stable Ruthenium-99 (Ru-99). This long-lived ground state of $^{99}Tc$ is considered practically stable with respect to Nuclear Medicine.

$^{99m}Tc$ is produced from the radioactive decay of its parent radioisotope Molbdenum-99 ($^{99}Mo$) which has a half-life of approximately 66 hours. $^{99m}Tc$ is used in approximately 85% of diagnostic imaging procedures in nuclear medicine worldwide. Currently, global demand for $^{99}Mo$ is met primarily by production through fission of Uranium-235 irradiated in a nuclear reactor or through a "neutron capture" nuclear reaction on Molybdenum-98. The $^{99}Mo$ is then purified and supplied routinely to manufacturers of $^{99}Mo/^{99m}Tc$ generators around the world. Its reasonably long half-life allows for transport to radiopharmacies over long distances without too much loss from nuclear decay. At the point and time of use, $^{99m}Tc$ is extracted from the $^{99}Mo/^{99m}Tc$ generator with a solvent, regularly with normal saline solution through a process called elution.

In addition, Rhenium-188 ($^{188}Re$) is used in Nuclear Medicine procedures and therapies and is derived from a Tungsten-188/Rhenium-188 ($^{188}W/^{188}Re$) generator.

The eluent from these types of $^{99m}Tc$ and $^{188}Re$ generators can be purified and concentrated with the technology and process of this disclosure.

The cost-effective utilization of a $^{99}Mo/^{99m}Tc$ generator and the quality of $^{99m}Tc$ based Single-Photon Emission Computed Tomography (SPECT) imaging diagnoses is controlled by the generator operation/elution management. The primary factor pertaining to the Nuclear Medicine diagnostic scans' quality is the concentration of the $^{99m}Tc$ in the $^{99}Mo/^{99m}Tc$ generator elution expressed as activity per mL. Hence, the useful life time of the $^{99}Mo/^{99m}Tc$ generator is dictated by the amount of $^{99}Mo$ remaining within the generator since it is the source of $^{99m}Tc$ via decay. The useful life of the generator can be extended by concentrating the $^{99m}Tc$ derived from the generator at any given time.

Generally, a $^{99m}Tc$ solution/eluate is produced from the $^{99}Mo/^{99m}Tc$ generator in fixed volume and the concentration of the $^{99m}Tc$ in the eluate decreases with the life time of the $^{99}Mo/^{99m}Tc$ generator due to the radioactive decay of the parent nuclide, $^{99}Mo$. Effective utilization of the $^{99}Mo/^{99m}Tc$ generator therefore, depends not only on the available $^{99m}Tc$ activity in the $^{99}Mo/^{99m}Tc$ generator, but also on the concentration of the $^{99m}Tc$ recovered in the eluted solution eluate, defined as activity per mL.

The present disclosure seeks to provide a radioisotope concentrator device for use with a radioisotope source, a system, and a process for capturing at least one radioisotope from a radioisotope solution obtained from a radioisotope source, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

BRIEF SUMMARY

According to a first aspect of the present disclosure, there is provided a radioisotope concentrator device for use with a radioisotope source, the radioisotope concentrator device comprises a concentrator column adapted for selectively capturing at least one radioisotope from a radioisotope solution obtained from the radioisotope source in use.

Preferably the radioisotope concentrator device is for use with a radioisotope source, the radioisotope concentrator device comprising a concentrator column adapted for selective catch-and-release of at least one radioisotope from a radioisotope solution obtained from a radioisotope source in use, a body having at least one injection port and at least one valve being configurable in at least two ways; wherein an eluent can be received through the concentrator column via the at least one injection port when the at least one valve of the radioisotope concentrator device is in a selected open configuration in use.

In a preferred form the body has at least one injection port and at least one valve configurable between a first open configuration to prevent fluid communication between the at least one injection port and the concentrator column for allowing fluid communication between the at least one competitive ion selective sorbent column, the concentrator column, and the radioisotope source in use, and a second open configuration for allowing fluid communication between the at least one injection port and the concentrator column, wherein the eluent can be received through the concentrator column via the at least one injection port when the at least one valve of the radioisotope concentrator device is in the second open configuration in use.

The fluid communication in one configurable way can be between one competitive ion selective sorbent column, the concentrator column, an injection device, a Millipore filter, and the radioisotope source in use which fluid communication is effected by a vacuum.

Preferably the vacuum is provided by the waste vial being connected to the exit of the concentrator device and the vacuum from the evacuated waste vial causing saline solution of radioisotope to be drawn into HCISS column, the concentration column and the waste vial.

Advantageously, the ability to selectively capture the at least one radioisotope on the concentrator column enables a radioisotope eluate solution to be produced that has a higher radioisotope concentration than the radioisotope solution obtained from the radioisotope source.

A radioisotope concentrator device can be applied to a radioisotope of Molybdenum/Technetium pairs for the separation/purification of Technetium from Molybdenum.

Also the radioisotope concentrator device can be applied to the radioisotope source of Tungsten/Rhenium in which the separation/purification is of Rhenium from Tungsten.

Preferably the disclosure provides a radioisotope concentrator device for use with a radioisotope source, the radioisotope concentrator device comprising: a concentrator column adapted for selectively catch-and-release at least one radioisotope from a radioisotope solution obtained from the radioisotope source in use, a body having at least one injection port and at least one valve being configurable between a first open configuration to prevent fluid communication between the at least one injection port and the concentrator column for allowing fluid communication between the at least one competitive ion selective sorbent column, the concentrator column, and the radioisotope source in use, a second open configuration for allowing fluid communication between the at least one injection port and the concentrator column, wherein an eluent can be received through the concentrator column via the at least one injection port when the at least one valve of the radioisotope concentrator device is in the second open configuration in use.

The fluid communication can be between one competitive ion selective sorbent column, the concentrator column, the injection device the Millipore filter, and the radioisotope source in use is effected by the vacuum The radioisotope source can be Molybdenum/Technetium pairs for the separation/purification of Technetium from Molybdenum or Tungsten/Rhenium the separation/purification is of Rhenium from Tungsten.

Preferably, the radioisotope concentrator device further comprises a body having an internal volume, the concentrator column being located substantially within the internal volume of the body in use.

Advantageously, the concentrator column being located substantially within the body reduces the risk of possible exposure to the radioisotope solution.

Preferably, the body comprises support means for supporting the concentrator column substantially within the internal volume of the body in use.

Preferably, the body comprises at least one entry port, the concentrator column being in fluid communication with the at least one entry port.

Advantageously, the concentrator column receives the radioisotope solution via the at least one entry port in use.

Preferably, the body further comprises at least one exit port, the concentrator column being in fluid communication with the at least one exit port.

Preferably, the radioisotope source is a radioisotope generator configured for generating the radioisotope solution.

Preferably, the radioisotope generator comprises an elution port, the radioisotope concentrator device further comprising a body having at least one entry port adapted for connecting to the elution port of the radioisotope generator in use.

Advantageously, the radioisotope concentrator device being connected directly to the radioisotope generator in use reduces the risk of possible loss of radioisotope solution.

Advantageously, the radioisotope concentrator device being connected directly to the radioisotope generator in use reduces the risk of possible exposure to the radioisotope solution.

Preferably, the elution port of the radioisotope generator comprises a needle device, the at least one entry port of the body of the radioisotope concentrator device comprising a septum adapted to receive at least a portion of the needle device therethrough when connecting the radioisotope concentrator device to the elution port of the radioisotope generator in use.

Advantageously, the use of a needle device and septum reduces the risk of possible exposure to the radioisotope solution.

Preferably, the radioisotope source is a vial comprising the radioisotope solution.

Preferably, the vial comprises a septum, the radioisotope concentrator device further comprising a body having at least one entry port equipped with a septum, each septum being adapted to receive at least a portion of a corresponding end of a double-ended hollow needle device when connecting the vial to the radioisotope concentrator device in use.

Preferably, the body is generally elongate having a bottom portion and a top portion, the at least one entry port being located at the bottom portion and the at least one exit port being located at the top portion.

Preferably, the at least one exit port comprises connecting means for connecting to an evacuated vial in use.

Preferably, the connecting means comprises a needle device to at least partially penetrate a septum of the evacuated vial in use.

Advantageously, the use of a needle device and septum reduces the risk of possible exposure to a radioisotope eluate solution comprising the at least one radioisotope.

Preferably, the body comprises shielding means for shielding at least the concentrator column in use.

Advantageously, the body comprising shielding means reduces the risk of possible exposure to the radioisotope solution in use.

Preferably, the body is generally elongate having a bottom portion, a top portion, and a wall portion extending between the bottom portion and the top portion, each of the bottom portion, the top portion, and the wall portion being manufactured from a radiation shielding material.

Advantageously, the top, bottom, and wall portions of the body being manufactured from a radiation shielding material to reduce the risk of possible exposure to the radioisotope solution in use.

Preferably, the radiation shielding material is lead or tungsten.

Preferably, the radioisotope concentrator device further comprises a competitive ion selective column adapted for removing at least one competitive ion from the radioisotope solution obtained from the radioisotope source in use.

Advantageously, the concentration of the radioisotope solution obtained from the radioisotope source can be increased by virtue of the competitive ion selective column selectively removing the at least one competitive ion from the radioisotope solution.

Preferably, the competitive ion selective column comprises a sorbent means for selectively capturing the at least one competitive ion in use.

Preferably, the competitive ion selective column is located upstream of the concentrator column.

Advantageously, competitive ionic species can be removed from the radioisotope solution by the competitive ion selective column before the solution reaches the concentrator column by virtue of the competitive ion selective column being located upstream of the concentrator column.

Preferably, the competitive ion selective column is in fluid communication with the concentrator column.

Preferably, the radioisotope concentrator device further comprises a body having an internal volume, the competitive ion selective column being located substantially within the internal volume of the body in use.

Advantageously, the competitive ion selective column being located substantially within the body reduces the risk of possible exposure to the radioisotope solution.

Preferably, the body comprises support means for supporting the competitive ion selective column substantially within the internal volume of the body in use.

Preferably, the body comprises at least one entry port, the competitive ion selective column being in fluid communication with the at least one entry port.

Advantageously, the competitive ion selective column receives the radioisotope solution via the at least one entry port in use.

Preferably, the at least one competitive ion is selected from the group of competitive ions comprising: a halide anion, and a breakthrough impurity ion.

Preferably, the halide anion is a chloride anion.

Advantageously, chloride ions within the radioisotope solution can be removed by the competitive ion selective column prior to the radioisotope solution reaching the concentrator column.

Preferably, the radioisotope source is a $^{99}$Mo/$^{99m}$Tc radioisotope generator, the radioisotope solution obtained from the $^{99}$Mo/$^{99m}$Tc radioisotope generator comprising a $^{99}$Mo breakthrough impurity ion.

Preferably, the radioisotope source is a $^{188}$W/$^{188}$Re radioisotope generator, the radioisotope solution obtained from the $^{188}$W/$^{188}$Re radioisotope generator comprising a $^{188}$W breakthrough impurity ion.

Preferably, the body comprises at least one injection port adapted to receive an injection device, the at least one injection port being operably connected to the concentrator column.

Preferably, the body further comprises a wall portion, the at least one injection port being located at the wall portion of the body.

Preferably, the injection device is adapted to receive an eluent for eluting through the concentrator column in use.

Advantageously, the at least one radioisotope can be eluted from the concentrator column by introducing an eluent via the at least one injection port in use.

Preferably, the radioisotope concentrator device further comprises at least one valve being configurable between a first open configuration for allowing fluid communication between the at least one injection port and the concentrator column to elute the at least one radioisotope from the concentrator column with an eluent and a second open configuration for allowing fluid communication between the competitive ion selective column and the concentrator column in use.

Advantageously, the at least one radioisotope can be selectively eluted from the concentrator column by introducing an eluent via the at least one injection port when the at least one valve is in the first open configuration in use.

Preferably, the body further comprises at least one exit port, the at least one valve being adapted for enabling fluid communication between the at least one injection port and the at least one exit port when the at least one valve is in the first open configuration.

Preferably, the body further comprises at least one entry port and at least one exit port, the at least one valve being adapted for enabling fluid communication between the at least one entry port and the at least one exit port when the at least one valve is in the second open configuration.

Preferably, the radioisotope concentrator device further comprises a body having an internal volume, at least a portion of the at least one valve being supported substantially within the internal volume of the body.

Advantageously, the at least portion of the at least one valve being located substantially within the body reduces the risk of possible exposure to the radioisotope solution in use.

Preferably, the radioisotope concentrator device further comprises an competitive ion selective column adapted for removing at least one competitive ion from the radioisotope solution obtained from the radioisotope source in use, the at least one valve being adapted for enabling fluid communication between the competitive ion selective column and the concentrator column when the at least one valve is in the second open configuration.

Advantageously, fluid communication of the radioisotope solution between the competitive ion selective column and the concentrator column is possible when the at least one valve is in the second open configuration.

Preferably, the at least one valve comprises a valve actuating means being configurable between a first position corresponding to the at least one valve being in the first open configuration and a second position corresponding to the at least one valve being in the second open configuration.

Advantageously, the at least one valve is transitioned between the first open configuration and the second open configuration by virtue of the valve actuating means.

Preferably, the valve actuating means is located externally of the body.

Advantageously, the valve actuating means being located externally of the body enables a user to manually transition the at least one valve between the first open configuration and the second open configuration by virtue of the valve actuating means.

Preferably, the valve actuating means comprises a handle.

Advantageously, the at least one valve is transitioned between the first open configuration and the second open configuration by virtue of a user manually actually the handle in use.

Preferably, the concentrator column comprises a sorbent means for selectively capturing the at least one radioisotope from the radioisotope solution obtained from the radioisotope source in use.

Advantageously, the at least one radioisotope is selectively captured from the radioisotope solution by virtue of the sorbent means.

Preferably, the sorbent means comprises either a multifunctional sorbent material (MFS) or an inorganic sorbent. Preferably, the multifunctional sorbent material is specified in Australia patent application AU2013903629, priority from which is claimed in PCT/AU2014/000920, published as WO/2015/039170 and incorporated by reference herein.

Preferably, the sorbents are selective to retarding ions selected from the group of ions comprising: pertechnetate [$^{99m}$TcO$_4^-$] anions and perrhenate [$^{188}$ReO$_4^-$] anions Advantageously, pertechnetate [$^{99m}$TcO$_4^-$] anions or perrhenate [$^{188}$ReO$_4^-$] anions are selectively retarded either on the MFS material or on the inorganic sorbent by virtue of fluidly communicating the corresponding radioisotope solution through the concentrator column in use.

Preferably, the sorbent means is selective to at least one radioisotope selected from the group of radioisotopes comprising: Tc-99m, and Re-188.

Advantageously, Tc-99m, or Re-188 is selectively retarded on the sorbent means by virtue of fluidly communicating the corresponding radioisotope solution through the concentrator column in use.

Preferably, the concentrator column comprises a generally elongate column body being adapted for operably connecting with each of the at least one entry port and the at least one exit port of the body of the radioisotope concentrator device to allow fluid communication through the column body in use.

Preferably, the column body comprises a bottom portion being adapted to operably connect to the at least one valve of the radioisotope concentrator device in use.

Preferably, the column body further comprises a top portion being adapted to connect to the at least one exit port of the body of the radioisotope concentrator device in use.

Preferably, the concentrator column comprises a generally elongate column body having an internal volume, the sorbent means being located substantially within the internal volume of the column body.

According to a second aspect of the present disclosure, there is provided a system for capturing at least one radioisotope from a radioisotope solution obtained from a radioisotope source, the system comprising:

a radioisotope source; and
a radioisotope concentrator device as defined in any one of the preceding paragraphs, the radioisotope concentrator device being operably connected to the radioisotope source to allow fluid communication therebetween in use.

Advantageously, the radioisotope solution obtained from the radioisotope source can be fluidly communicated to the radioisotope concentrator device by virtue of the operable connection between the source and the device.

Preferably, the radioisotope source is a radioisotope generator configured for generating the radioisotope solution.

Preferably, the radioisotope generator comprises an elution port, the radioisotope concentrator device comprising a body having at least one entry port adapted for connecting to the elution port of the radioisotope generator in use.

Advantageously, the radioisotope solution generated by the radioisotope generator is fluidly communicated from the elution port to the at least one entry port of the radioisotope concentrator device by virtue of the operable connection between the two devices.

Preferably, the elution port of the radioisotope generator comprises a needle device, the at least one entry port of the body of the radioisotope concentrator device comprising a septum adapted to receive at least a portion of the needle device therethrough when connecting the radioisotope concentrator device to the elution port of the radioisotope generator in use.

Advantageously, the use of a needle device and septum reduces the risk of possible exposure to the radioisotope solution in use.

Preferably, the radioisotope source is a vial comprising the radioisotope solution.

Preferably, the vial comprises a septum and the radioisotope concentrator device comprises a body having at least one entry port equipped with a septum, the system further comprising a double-ended hollow needle device, each septum being adapted to receive at least a portion of a corresponding end of the double-ended hollow needle device when connecting the vial to the radioisotope concentrator device in use.

Preferably, the radioisotope concentrator device comprises a body having at least one exit port, the system further comprising a radioisotope collecting means adapted for operably connecting to the at least one exit port of the body of the radioisotope concentrator device to allow fluid communication therebetween in use.

Advantageously, the radioisotope collecting means is operably connected to the at least one exit port of the body of the radioisotope concentrator device to enable the at least one radioisotope to be collected from the concentrator column in use.

Preferably, the at least one exit port of the body of the radioisotope concentrator device comprises a needle device, the radioisotope collecting means comprising a septum adapted for receiving at least a portion of the needle device therethrough to allow fluid communication therebetween in use.

Advantageously, the use of a needle device and septum reduces the risk of possible exposure to the at least one radioisotope in use.

Preferably, the radioisotope collecting means comprises an evacuated vial, the evacuated vial comprising the septum.

Advantageously, the at least one radioisotope is collected as a radioisotope eluate solution within the evacuated vial when the vial is operably connected to the at least one exit port of the body of the radioisotope concentrator device in use.

Advantageously, the at least one radioisotope is collected as a radioisotope eluate solution within the evacuated vial by virtue of the negative pressure that is applied to the at least one exit port when the evacuated vial is operably connected to the at least one exit port of the body of the radioisotope concentrator device in use.

Preferably, the radioisotope collecting means further comprises shielding means for shielding the evacuated vial in use.

Advantageously, the radioisotope collecting means comprising shielding means reduces the risk of possible exposure to the radioisotope eluate solution in use.

Preferably, the radioisotope collecting means comprises housing for receiving at least a portion of the evacuated vial therein.

Preferably, the housing is manufactured from a radiation shielding material.

Advantageously, the housing being manufactured from a radiation shielding material reduces the risk of possible exposure to the radioisotope eluate solution in use.

Preferably, the radiation shielding material is lead or tungsten.

Preferably, the radioisotope concentrator device comprises a body having at least one exit port, the system further comprising a waste collecting means adapted for operably connecting to the at least one exit port of the body of the radioisotope concentrator device to allow fluid communication therebetween in use.

Advantageously, the waste collecting means is operably connected to the at least one exit port of the body of the radioisotope concentrator device to enable the waste from the radioisotope solution to be collected in the waste collecting means after the at least one radioisotope has been selectively captured on the concentrator column in use.

Preferably, the waste collecting means comprises an evacuated vial, the evacuated vial comprising a septum adapted for receiving at least a portion of the needle device therethrough to allow fluid communication therebetween in use.

Advantageously, the waste from the radioisotope solution is collected within the evacuated vial when the vial is operably connected to the at least one exit port of the body of the radioisotope concentrator device in use.

Advantageously, the waste from the radioisotope solution is collected within the evacuated vial by virtue of the negative pressure that is applied to the at least one exit port when the evacuated vial is operably connected to the at least one exit port of the body of the radioisotope concentrator device in use.

Preferably, the radioisotope concentrator device comprises a body having at least one injection port and at least one valve being configurable between a first open configuration to prevent fluid communication between the at least one injection device and the concentrator column and a second open configuration for allowing fluid communication between the at least one injection port and the concentrator column in use, the system further comprising an injection device comprising an eluent for eluting through the concentrator column via the at least one injection port when the at least one valve of the radioisotope concentrator device is in the second open configuration in use.

Advantageously, the at least one radioisotope can be selectively eluted from the concentrator column by introducing an eluent via the at least one injection port when the at least one valve is in the second open configuration in use.

According to a third aspect of the present disclosure, there is provided a radioisotope concentrator device for use with a radioisotope source, the radioisotope concentrator device comprising:
  a body having an internal volume;
  a concentrator column disposed within the internal volume, the concentrator column being adapted for selectively capturing at least one radioisotope from a radioisotope solution obtained from the radioisotope source in use; and
  a competitive ion selective column disposed within the internal volume, the competitive ion selective column being adapted for removing at least one competitive ion from the radioisotope solution obtained from the radioisotope source in use.

Advantageously, the ability to selectively capture the at least one radioisotope on the concentrator column enables a radioisotope eluate solution to be produced that has a higher radioisotope concentration than the radioisotope solution obtained from the radioisotope source.

Preferably, the competitive ion selective column is located upstream of the concentrator column.

Advantageously, the purity of the radioisotope solution generated by the radioisotope generator can be increased before the radioisotope solution reaches the concentrator column by virtue of the competitive ion selective column being located upstream of the concentrator column.

Preferably, the body comprises at least one entry port, the at least one entry port being in fluid communication with the internal volume.

Preferably, the body further comprises at least one exit port, the at least one exit port being in fluid communication with the internal volume.

Preferably, the radioisotope source is a radioisotope generator configured for generating the radioisotope solution.

Preferably, the radioisotope generator comprises an elution port, the body further comprising at least one entry port being in fluid communication with the internal volume, the at least one entry port being adapted for connecting to the elution port of the radioisotope generator in use.

Preferably, the radioisotope source is a vial comprising the radioisotope solution.

Preferably, the vial comprises a septum, the body further comprising at least one entry port equipped with a septum, the at least one entry port being in fluid communication with the internal volume, each septum being adapted to receive at least a portion of a corresponding end of a double-ended hollow needle device when connecting the vial to the radioisotope concentrator device in use.

Preferably, the at least one exit port comprises connecting means for connecting to an evacuated vial in use.

Preferably, the body comprises at least one injection port adapted to receive an injection device, the at least one injection port being operably connected to the concentrator column.

[1] Preferably, the radioisotope concentrator device further comprises at least one valve being configurable between a first open configuration for allowing fluid communication between the competitive ion selective column and the concentrator column in use and a second open configuration for allowing fluid communication between the at least one injection port and the concentrator column in use to elute the at least one radioisotope from the concentrator column with an eluent.

Preferably, the body further comprises at least one exit port, the at least one valve being adapted for enabling fluid communication between the at least one injection port and the at least one exit port when the at least one valve is in the second open configuration.

Preferably, the body further comprises at least one entry port and at least one exit port, the at least one valve being adapted for enabling fluid communication between the at least one entry port and the at least one exit port when the at least one valve is in the first open configuration in use.

According to a fourth aspect of the present disclosure, there is provided a process for capturing at least one radioisotope from a radioisotope solution obtained from a radioisotope source using a radioisotope concentrator device, the process comprising the step of:
  fluidly communicating a radioisotope solution from the radioisotope source through a concentrator column to capture the at least one radioisotope on the concentrator column.

Advantageously, the ability to selectively capture the at least one radioisotope on the concentrator column enables a radioisotope eluate solution to be produced that has a higher radioisotope concentration than the radioisotope solution obtained from the radioisotope source.

Preferably, the radioisotope source is a radioisotope generator configured for generating the radioisotope solution, the radioisotope generator comprising an elution port, the radioisotope concentrator device comprising a body having at least one entry port adapted for connecting to the elution port of the radioisotope generator in use, the process further comprising the step of:
  operably connecting the at least one entry port of the body of the radioisotope concentrator device to the elution port of the radioisotope generator.

Preferably, the radioisotope source is a vial comprising the radioisotope solution, the vial being equipped with a septum, the radioisotope concentrator device comprising a body having at least one entry port equipped with a septum each septum being adapted to receive at least a portion of a corresponding end of a double-ended hollow needle device when connecting the vial to the radioisotope concentrator device in use, the process further comprising the step of:
  operably connecting the vial to the at least one entry port of the body of the radioisotope concentrator device by virtue of the double-ended hollow needle device.

Preferably, the radioisotope concentrator device comprises a competitive ion selective column located upstream of the concentrator column, the process further comprising the step of:

fluidly communicating the radioisotope solution through the competitive ion selective column to remove at least one competitive ion from the radioisotope solution.

Advantageously, the purity of the radioisotope solution generated by the radioisotope generator can be increased before the radioisotope solution reaches the concentrator column by virtue of the competitive ion selective column being located upstream of the concentrator column.

Preferably, the process further comprises the step of:
receiving within a waste collecting means a radioisotope eluate solution remaining after the at least one radioisotope has been captured on the concentrator column.

Preferably, the radioisotope concentrator device comprises a body having at least one exit port, the waste collecting means being adapted for operably connecting to the at least one exit port of the body of the radioisotope concentrator device to allow fluid communication therebetween in use, the process further comprising the step of:
operably connecting the waste collecting means to the at least one exit port of the body of the radioisotope concentrator device.

Preferably, the waste collecting means comprises an evacuated vial, the process further comprising the step of:
fluidly communicating the radioisotope eluate solution to the waste collecting means under a negative pressure corresponding to the pressure within the evacuated vial.

Advantageously, the waste from the radioisotope solution is collected within the evacuated vial by virtue of the negative pressure that is applied to the at least one exit port when the evacuated vial is operably connected to the at least one exit port of the body of the radioisotope concentrator device in use.

Preferably, the process further comprises the step of:
fluidly communicating an eluent through the concentrator column to elute the at least one radioisotope from the concentrator column.

Advantageously, the at least one radioisotope can be selectively eluted form the concentrator column using an eluent to produce a radioisotope eluate solution.

Preferably, the process further comprises the step of:
receiving within a radioisotope collecting means the at least one radioisotope eluted from the concentrator column with the eluent.

Advantageously, the at least one radioisotope can be selectively eluted form the concentrator column using an eluent to produce a radioisotope eluate solution for collecting within the radioisotope collecting means.

Preferably there is provided a general process 700 using a radioisotope concentrator device 20 for selectively capturing radioisotopes from a highly dilute saline solution of radioisotopes eluted from the radioisotope generator 100 and then eluting the captured radioisotopes from the radioisotope concentrator device 20 as a pure and more concentrated saline solution of the desired radioisotopes by the radioisotope concentrator device 20 being configured for selectively capturing isotope from the saline solution eluted from the radioisotope generator 100 by the stationary phase packed within the column body 210 of the concentrator column 200 being either a multifunctional sorbent material or an inorganic sorbent selective to retard the radioisotope anions wherein the method includes the steps of:
the radioisotope concentrator having a valve, wherein with the valve is placed in a first position 710 such that the valve 400 is in the first open configuration and the HCISS column 300, the concentrator column 200, and the evacuated vial 610 being in fluid communication:

In a first step 715, the cylindrical entry port 34e of the assembled radioisotope concentrator device 20 and its self-aligning port is inserted into an elution port 110 of the radioisotope generator 100 at the bottom portion 314 of the HCISS column body 310.

In a second step 720, the evacuated vial 610 of the waste collecting means is inverted and then inserted into the exit port 32e of the body 30 of the concentrator device 20 and the its self-aligning port enables fluid communication between the concentrator column 200 and the evacuated vial 610.

The a third step 735 has the vacuum within the evacuated vial 610 imparting a negative pressure on the system 10 causing the saline solution of radioisotope to be drawn up through the HCISS column 300 and the concentration column 200 into the vial 610.

In step 740 in this arrangement, the HCISS column 300 comprises a stationary phase that allows removing the competitive ions from the eluate solution and consecutively to allows selective capture (catching) of the desired radioisotope on either a multifunctional sorbent material or an inorganic sorbent in the concentrator column 200.

The remaining eluate solution is captured within the vial 610 as non-radioactive effluent waste in step 745.

The next step 750, the Millipore filter housed in a self-aligning insertion device is inserted into the exit port 32a of the body 30 of the concentrator device 20.

In a further step 755 has the radioisotope concentrator valve rotated to the second position such that the valve 400 is in the second open configuration and the injection device 45, the concentrator column 200, the Millipore filter 535, and the evacuated round bottom vial 510 of the pure and concentrated radioisotope solution collecting means 500 being in fluid communication wherein In step 755, the evacuated vial 510 of the radioisotope collecting means is placed within the housing 500 and sealed and the sealed housing 500 is then inverted and inserted into the exit port 32e of the body 30 of the radioisotope concentrator device 20;

The insertion device at the exit port 32e penetrates the evacuated vial 510 in step 760 to enable fluid communication between the injection device 45, the concentrator column 200, and the evacuated vial 510;

And in steps 765 and 770 the vacuum within the evacuated vial 510 imparts a negative pressure on the system 10 causing the low volume saline solution to be drawn up from the injection device 45 into the vial 510 via the concentrator column 200 and allows the concentrator column 200 to elute (release) the selectively captured radioisotope anions from the concentrator column 200;

whereby the output 780 is the resulting low volume post-elution saline solution radioisotope in the vial 510 can be used for radio-labelling an organ-specific pharmaceutical or used directly without pharmaceutical tagging for specific procedures requiring only the radioisotope anions as the primary radiopharmaceutical.

Preferably, the radioisotope concentrator device comprises a body having at least one exit port, the radioisotope collecting means being adapted for operably connecting to the at least one exit port of the body of the radioisotope concentrator device to allow fluid communication therebetween in use, the process further comprising the step of:
operably connecting the radioisotope collecting means to the at least one exit port of the body of the radioisotope concentrator device.

Preferably, the radioisotope collecting means comprises an evacuated vial, the process further comprising the step of:

fluidly communicating the at least one radioisotope to the waste radioisotope means under a negative pressure corresponding to the pressure within the evacuated vial.

Advantageously, the at least one radioisotope is collected as a radioisotope eluate solution within the evacuated vial by virtue of the negative pressure that is applied to the at least one exit port when the evacuated vial is operably connected to the at least one exit port of the body of the radioisotope concentrator device in use.

Preferably, the eluent comprises a saline solution.

Advantageously, the at least one radioisotope is eluted form the concentrator column using saline solution.

Preferably, the volume of saline solution used to elute the at least one radioisotope from the concentrator column is in the range from approximately 0.1 mL to approximately 2.0 mL.

Advantageously, the concentration of the at least one radioisotope within the radioisotope eluate solution is higher than the concentration of the at least one radioisotope in the radioisotope solution eluted from the radioisotope generator.

Tungsten/Rhenium and Molybdenum/Technetium pairs being chemical analogues, and the separation/purification of Rhenium from Tungsten is chemically analogous to the separation/purification of Technetium from Molybdenum Other aspects of the invention are also disclosed.

BRIEF DESCRIPTION OF THE SEVERAL VIEWS OF THE DRAWINGS

Notwithstanding any other forms which may fall within the scope of the present disclosure, preferred embodiments of the disclosure will now be described, by way of example only, with reference to the accompanying drawings and examples in which.

DETAILED DESCRIPTION

Figure 1:
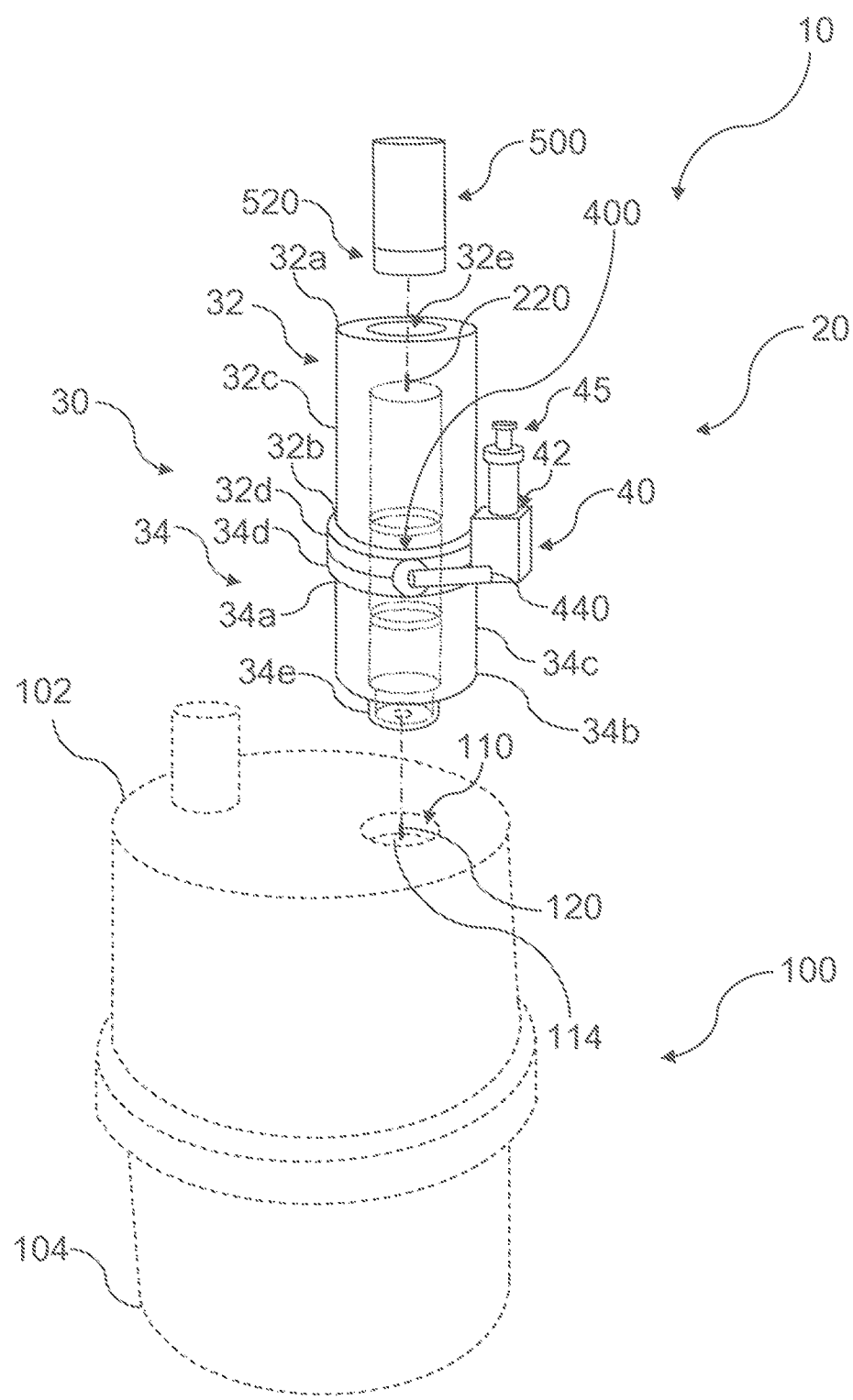
FIG. 1 shows a perspective view (in exploded form) of a system comprising a radioisotope concentrator device for capturing radioisotopes from a radioisotope solution generated by a radioisotope generator (shown in dashed outline) according to a preferred embodiment of the present disclosure.

It should be noted in the following description that like or the same reference numerals in different embodiments denote the same or similar features.

FIG. 1 shows a system 10 comprising a radioisotope concentrator device 20 configured for use with a radioisotope source in the form of a radioisotope generator 100 (shown in dashed outline) for selectively capturing radioisotopes from a radioisotope solution generated by the radioisotope generator 100 according to a preferred embodiment of the present disclosure.

In this embodiment, the radioisotope concentrator device 20 is provided in the form of housing and a group of interconnectable sterile components which are configured to be supported as a single unit within the housing in use. Advantageously, the single unit is a sterile disposable cartridge.

Housing

In relation to the housing, the concentrator device 20 comprises two generally cylindrical portions, a first body portion 32 and a second body portion 34, that are adapted to couple together in use to define a generally elongate cylindrical body 30. Advantageously, the cylindrical portions of the housing are of multiple uses. For each use, one sterile disposable cartridge (single unit) is inserted into the housing.

The first body portion 32 comprises a top end portion 32a and a bottom end portion 32b and a wall portion 32c extending between the top end portion 32a and the bottom end portion 32b. The top end portion 32a, bottom end portion 32b and wall portion 32c together define a generally hollow cylindrical cavity. Located at the bottom end portion 32b is a flange portion 32d that extends outwardly and generally laterally from the wall portion 32c. The top end portion 32a, the bottom end portion 32b, and the wall portion 32c are each manufactured from a radiation shielding material to afford the first body portion 32 with shielding means to shield a user from exposure to any radioactive material located within the first body portion 32. In this embodiment, the radiation shielding material is lead or tungsten.

Located at the top end portion 32a of the first body portion 32 is a generally circular opening in the form of an exit port 32e.

The second body portion 34 comprises a top end portion 34a and a bottom end portion 34b, and a wall portion 34c extending between the top end portion 34a and the bottom end portion 34b. The top end portion 34a, bottom end portion 34b and wall portion 34c together define a generally hollow cylindrical cavity. Located at the top end portion 34a is a flange portion 34d that extends outwardly and generally laterally from the wall portion 34c.

The top end portion 34a, the bottom end portion 34b, and the wall portion 34c are each manufactured from a radiation shielding material to afford the second body portion 34 with shielding means to shield a user from exposure to any radioactive material located within the second body portion 34. In this embodiment, the radiation shielding material is lead or tungsten.

Located at the bottom end portion 34b is a generally cylindrical hollow portion in the form of an entry port 34e that extends downwardly from the bottom end portion 34b. The cylindrical entry port 34e has an external diameter that is smaller than the external diameter of the second body portion 34.

The flange portion 32d of the first body portion 32 and the flange portion 34d of the second body portion 34 each comprise first and second locking apertures (not shown) located at opposing sides of the corresponding flange portion 32d and 34d. Each of the first and second locking apertures are oriented generally parallel to the longitudinal axis of the concentrator device 10 and extend substantially through the corresponding flange portion 32d and 34d from the upper surface of the flange portion to the lower surface.

Figure 2:
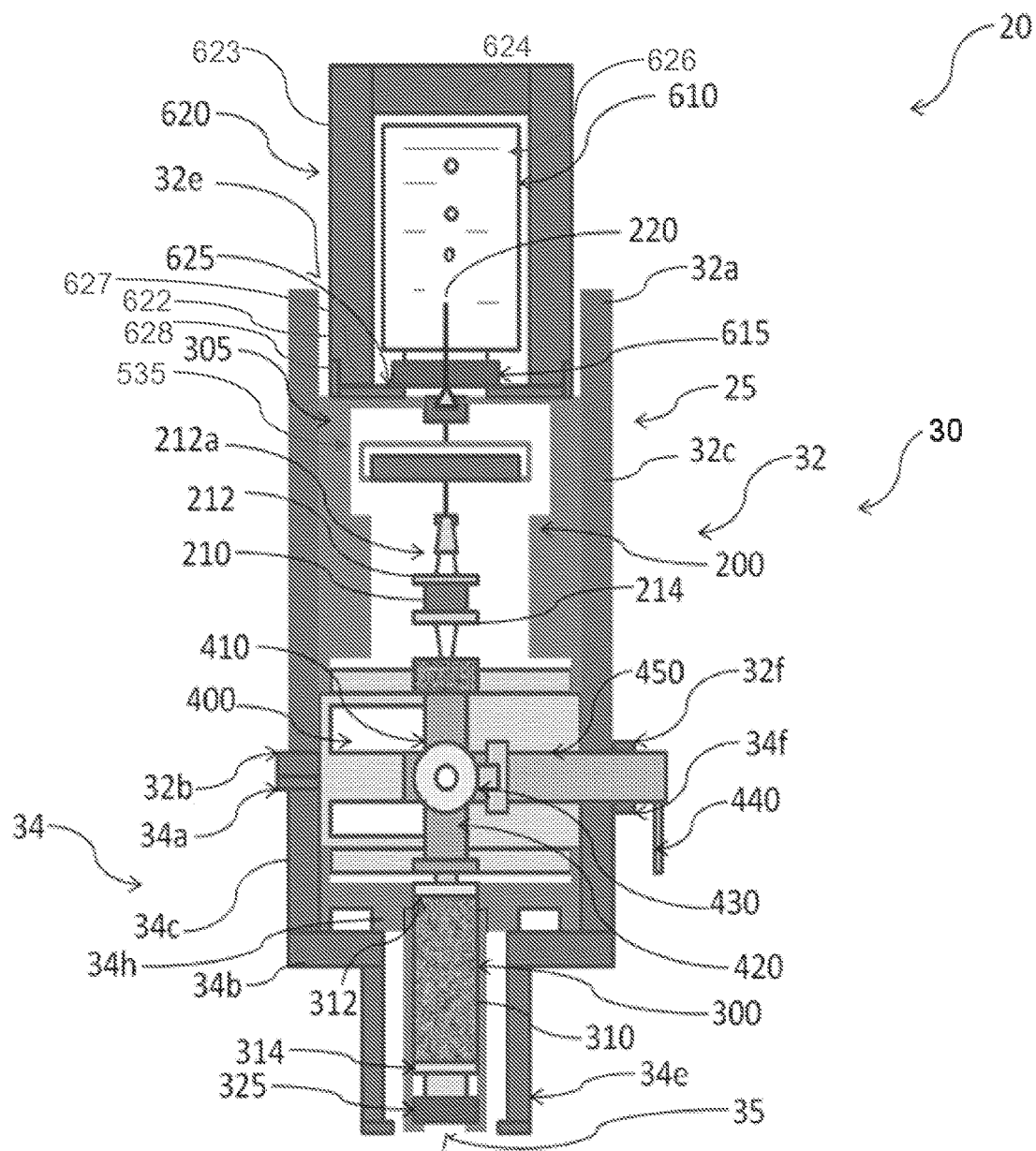
FIG. 2 shows a cross-sectional view of the radioisotope concentrator device of FIG. 1.

As shown in FIG. 2, the flange portion 32d of the first body portion 32 and the flange portion 34d of the second body portion 34 each further comprise a generally semicircular aperture 32f and 34f that extends substantially through the corresponding portion of the wall portion 32c and 34c into the respective internal cavity of the first body portion 32 and the second body portion 34.

Sterile Components

In relation to the sterile components configured to be supported as a single unit (sterile disposable cartridge) within the body 30 of the radioisotope concentrator device 20, the four main interconnectable sterile components include: an injection device, a concentrator column 200, a competitive ion selective column 300, and a valve 400 operably connecting the concentrator column 200 to the competitive ion selective column 300 in use.

Injection Device

Figure 3:
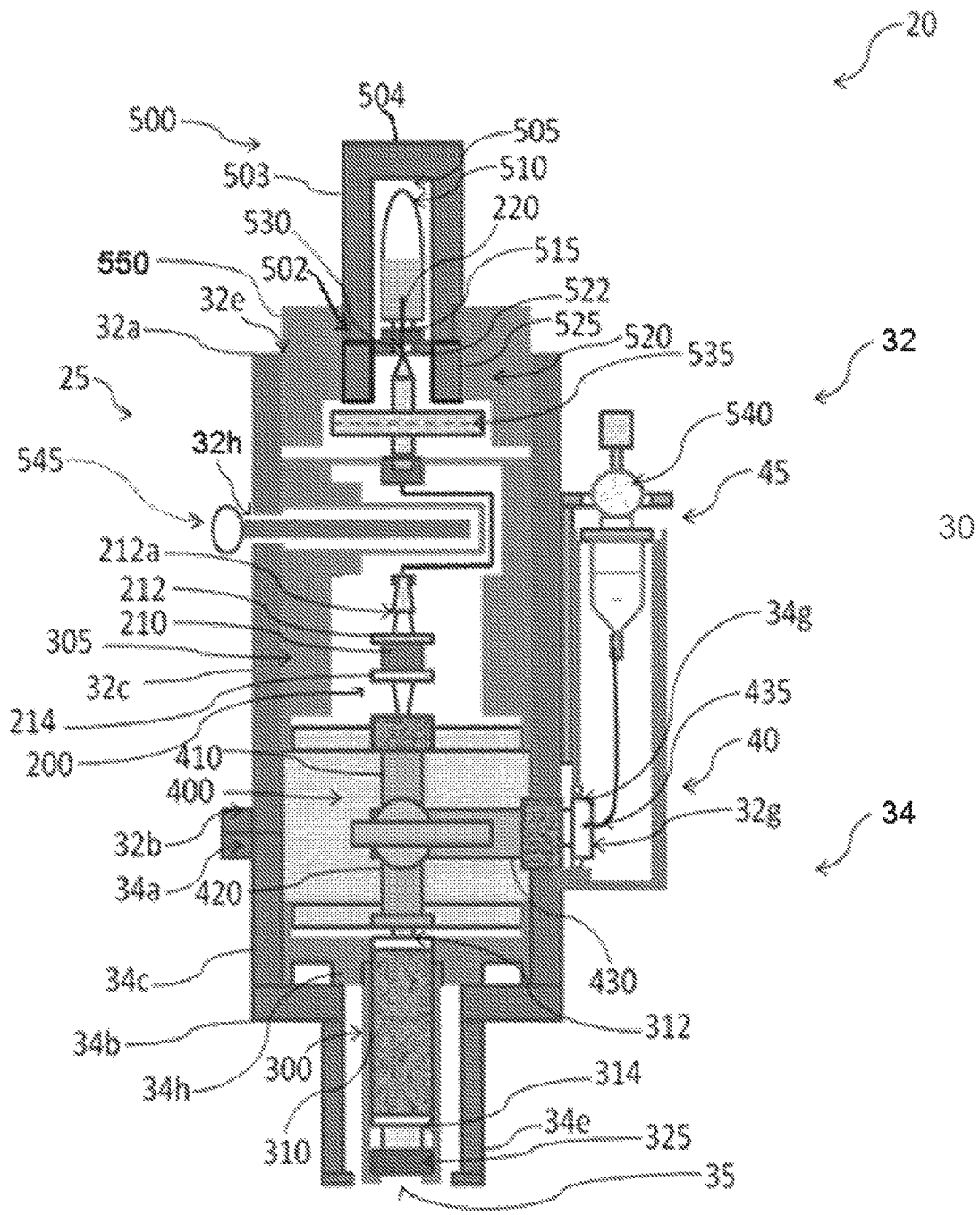
FIG. 3 shows a second cross-sectional side view of the radioisotope concentrator device of FIG. 1.
Figure 4:
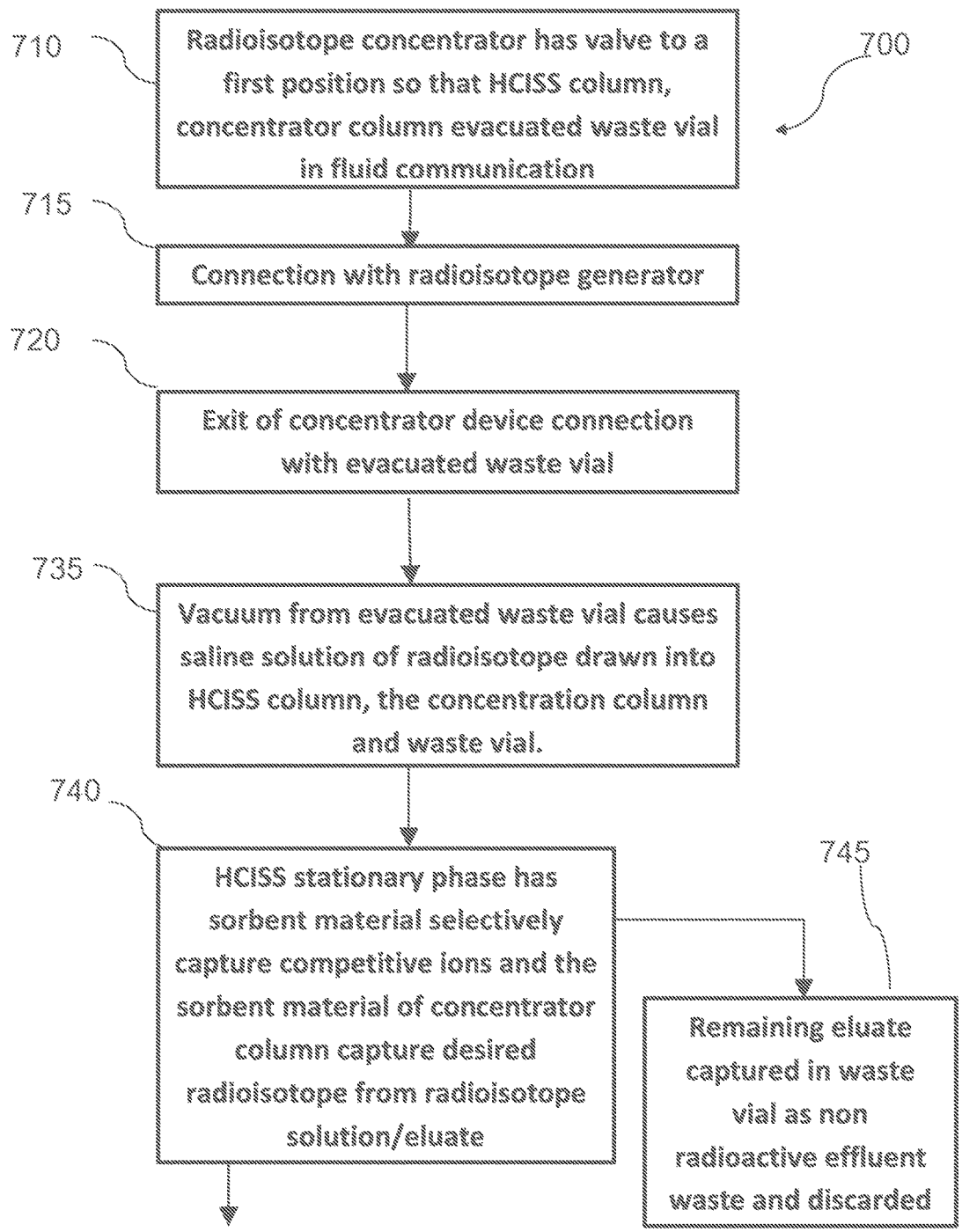
FIGS. 4 and 5 are diagrammatic flow diagrams of the process for producing a concentrated radioisotope eluate solution in accordance with a preferred embodiment of the present disclosure.

As shown in FIG. 3, the flange portion 32d of the first body portion 32 and the flange portion 34d of the second body portion 34 each further comprise an additional generally semicircular aperture 32g and 34g that extends substantially through the corresponding portion of the wall portion 32c and 34c to the internal cavity of the first body portion 32 and the second body portion 34, respectively. Affixed to the wall portion 34c of the second body portion 34 at the location of the generally semicircular aperture 34g is an injection port 40 for use in mounting an injection device 45 to the concentrator device 20. The injection port 40 comprises an opening 42 to receive and support the injection device 45 therein. The inlet port of the injection device 45 is fitted with an air inlet which is vented to the atmosphere with a sterilizing (0.22 micron) filter 540 to ensure that the sterility of the system 10 is not compromised while allowing air to pass through the fluid flow thus assuring complete withdrawal of all liquid and the radioisotopes dissolved therein through the system 10.

In this arrangement, the first and second body portions 32 and 34 are brought together such that their respective flange portions 32d and 34d are substantially engaged. The first and second locking apertures in the flange portion 32d of the first body portion 32 are aligned with the corresponding first and second locking apertures in the flange portion 34d of the second body portion 34 and a bolt (not shown) is passed through each of the aligned pairs of first and second locking apertures to lock the first body portion 32 and the second body portion 34 together to form the body 30 of the concentrator device 20 having a generally cylindrical shape and an internal volume 305.

The radioisotope generator 100 used may be any type of commercially available generator that comprises an elution port to enable the radioisotope concentrator device 20 to be mounted thereto.

In this embodiment, and as shown in FIG. 1, the radioisotope generator 100 (shown in dashed outline) comprises a generally cylindrical body having a top end portion 102 and an opposing bottom end portion 104. Located at the top end portion 102 is a generally circular recess in the form of an elution port 110 that extends part way down from the top end portion 102 to terminate in a generally circular base 114. Extending upwardly through the base 114 is a needle device in the form of a hollow spike or needle 120 oriented generally orthogonally to the base 114. The tip of the needle 120—terminates below the top end portion 102 of the radioisotope generator 100. In use, the radioisotope solution generated by the radioisotope generator 100 passes through the hollow needle 120 to exit the elution port 110.

The internal diameter of the elution port 110 is larger than, but complementary to, the external diameter of the cylindrical entry port 34e of the second body portion 34 of the concentrator device 20. In this arrangement, the elution port 110 is configured to receive the entry port 34e of the second body portion 34 therein when the concentrator device 20 is mounted to the radioisotope generator 100 in use.

The entry port 34e of the second body portion 34 of the body 30 of the radioisotope concentrator device 20 comprises an aperture 35.

Concentrator Column

As shown in FIGS. 2 and 3, the concentrator column 200 is a chromatographic column configured for selectively capturing the desired radioisotopes from the radioisotope solution eluted from the radioisotope generator 100 in use. The concentrator column 200 comprises a generally elongate hollow column body 210 having a top portion 212 and an opposing bottom portion 214. Packed within the hollow column body 210 is a suitable sorbent means or stationary phase (not shown) for selectively capturing the desired radioisotopes.

Located at the top portion 212 of the column body 210 is a hollow spigot 212a which is in fluid communication with the hollow column body 210. Mounted to the spigot 212a is a hollow syringe needle 220 which is oriented generally parallel to the longitudinal axis of the column body 210. The bottom portion 214 of the column body 210 comprises an internally threaded portion (not shown).

Competitive Ion Selective Column

As shown in FIGS. 2 and 3, the competitive ion selective column 300 is configured for selectively removing competitive ions such as, for example, interfering/competing halide anions like chloride anions present within the saline solution, and molybdate (Mo-99) or tungstate (W-188) ions associated with a corresponding Mo-99 or W-188 breakthrough that may occur in the radioisotope solution eluted from the corresponding Mo-99/Tc-99m or W-188/Re-188 radioisotope generator 100 in use. Such competitive ions will compete with the corresponding Tc-99m or Re-188 radioisotope for adsorption on the concentrator column 200, thereby reducing the overall concentration of the final radioisotope solution. The competitive ion selective column 300, hereafter referred to as the Halide and Competitive Ion Selective Sorbent (HCISS) column 300, comprises a generally elongate hollow column body 310 having a top portion 312 and an opposing bottom portion 314. Packed within the hollow column body 310 of the HCISS column 300 is a suitable stationary phase (not shown) for selectively removing the desired halide anion impurities from the eluted radioisotope solution.

The top portion 312 of the HCISS column body 310 comprises a male luer connection (not shown). The bottom portion 314 of the column body 310 has an external diameter that is of suitable dimension to locate within the hollow cylindrical entry port 34e of the second body portion 34 of the concentrator device 20.

In this arrangement, when the concentrator column 200, the HCISS column 300, and the valve 400 are all connected together, the interconnected sterile components are supported as a single unit substantially within the internal volume 305 of the body 30 of the concentrator device 20 by virtue of the top portion 312 of the HCISS column body 310 being supported on the inner wall surface 34h of the bottom end portion 34b of the second body portion 34 such that the bottom portion 314 of the HCISS column body 310 locates within the internal cavity of the hollow cylindrical entry port 34e.

The bottom portion 314 of the HCISS column body 310 comprises at a terminal end thereof, a septum 325.

Valve

As shown in FIGS. 2 and 3, the valve 400 is a three-way valve comprising a first end portion 410, a second end portion 420, and a third end portion 430. The first end portion 410 comprises an externally threaded portion (not shown) which is complementary to the internally threaded portion at the bottom portion 214 of the concentrator column body 210 to enable the concentrator column 200 to be operably connected to the valve 400. The second end portion 420 of the valve 400 comprises a female luer connection (not shown) which is complementary to the male luer connection at the top portion 312 of the HCISS column body 310 to enable the HCISS column 300 to be operably connected to the valve 400.

The third end portion 430 of the valve 400 is connected via an elongate tube 435 to the injection device 45 mounted within the opening 42 of the injection port 440 to enable the injection device 45 to be operably connected to the valve 400.

As shown in FIG. 3, the injection device 45 is in the form of a syringe that is configured to comprise a suitable eluent such as, for example, saline solution.

The valve 400 further comprises a valve actuating means in the form of a handle or lever 440. The lever 440 is operably connected at a terminal end thereof to the valve 400 by virtue of an elongate pin 450.

In this arrangement, the valve 400 is configurable between a first open configuration for allowing fluid communication between the injection device 45 and the concentrator column 200 to elute selectively captured radioisotopes from the concentrator column 200 with the saline solution eluent and a second open configuration to prevent fluid communication between the injection device 45 and the concentrator column 200, but to allow fluid communication between the HCISS column 300 and the concentrator column 200. The valve 400 is manually operated by virtue of the lever 440, which is configurable between a first position corresponding to the valve 400 being in the first open configuration and a second position corresponding to the valve 400 being in the second open configuration.

When the first and second body portions 32 and 34 of the cylindrical body 30 of the concentrator device 20 are brought together to enclose the interconnected sterile components within the internal volume 305 of the body 30, the flange portions 32d and 34d substantially engage, such that the first set of semicircular apertures 32f and 34f of the corresponding first body portion 32 and the second body portion 34 align to form a first generally circular aperture, and the second set of semicircular apertures 32g and 34g align to form a second generally circular aperture. The first, second and third end portions 410, 420, and 430 of the valve 400 are supported substantially within the internal volume 305 of the body 30 of the concentrator device 20, and the pin 450 of the valve 400 extends outwardly from the internal volume 305 of the body 30 through the circular aperture defined by the first set of semicircular apertures 32f and 34f such that the lever 440 is located externally of the body 30. The elongate tube 435 extends outwardly from the internal volume 305 of the body 30 through the circular aperture defined by the second set of semicircular apertures 32g and 34g to operably connect with the injection device 45 at the injection port 40.

As shown in FIGS. 2 and 3, when the three main interconnectable sterile components of the radioisotope concentrator device 20 are operably connected together and supported within the internal volume 305 of the body 30, the HCISS column 300 is located upstream of the concentrator column 200.

In this arrangement, the concentrator column 200 is in direct fluid communication with the exit port 32e of the radioisotope concentrator device 20 by virtue of the needle 220 being located within the entry port 32e. The concentrator column 200 is also in fluid communication with the entry port 34e of the radioisotope concentrator device 20 by virtue of the operable connection between the concentrator column 200 and the HCISS column 300 when the valve 400 is in the second open configuration to enable fluid communication.

Radioistope Collecting Means

As shown in FIG. 3, the system 10 further comprises a radioisotope collecting means in the form of a housing 500 and an evacuated vial 510 sealed with a septum 515 which is configured to be received within the housing 500 in use. A sterilizing (0.22 micron) filter 535 is fitted between the septum 515 and the concentrator column 200 to ensure that the sterility of the system 10 is not compromised.

The housing 500 comprises a generally circular base portion 504 and a wall portion 503 extending upwardly from the base portion 504 and terminating at a top portion 502 to define a generally cylindrical shaped housing 500 with an internal volume 505.

The evacuated vial 510 can be sealed within the housing 500 by virtue of a cap 520 that can be applied to the top portion 502 of the housing 500. The cap 520 comprises a generally circular top portion 522 and a skirt portion 525 disposed around the periphery of the top portion 522. The top portion 502 of the housing 500 has a slightly smaller external diameter than the base portion 504 and comprises an externally threaded portion (not shown). The skirt portion 525 of the cap 520 comprises a complementary internally threaded portion (not shown) to meshingly engage the externally threaded portion at the top portion 502 of the housing 500 to seal the vial 510 within the housing 500 in use.

The cap 520 comprises an aperture 530 extended substantially through the circular top portion 522. The aperture 530 is smaller in diameter than the diameter of the evacuated vial 510 to prevent the vial 510 from falling out through the aperture 530 of the cap 520 when the sealed housing 500 is inverted in use. The aperture 530 provides access to the septum 515 of the evacuated vial 510 in use.

The housing 500 and the cap 520 are both manufactured from a radiation shielding material such as lead or tungsten to shield users from exposure to any radioisotopes collected within the vial 510 once eluted from the concentrator column 200.

The system 10 further comprises a generally cylindrical sheath 550 that is configured to act as an adaptor to enable at least the top portion 502 of the housing 500 and the cap 520 to fit snugly within the exit port 32e located at the top end portion 32a of the first body portion 32 in use. The sheath 550 comprises an internal diameter that is complementary to the external diameters of the cap 520 and the housing 500, and an external diameter that is complementary to the internal diameter of the exit port 32e. In this embodiment, the sheath 550 is manufactured from a suitable engineering polymer such as, for example, high density polyethylene (HDPE) or polytetrafluoroethylene (PTFE).

The system 10 further comprises shielding means in the form of a generally elongate shield plate 545 that is configured for inserting through a slot 32h extending substantially through the wall portion 32c at the top end portion 32a of the first body portion 32. In use, the shield plate 545 is located into the radiation path to shield the skyshine stream from the concentrator column 200 when the radioisotope (Tc-99m) is loaded onto the inorganic sorbent.

The shield plate 545 is manufactured from a radiation shielding material such as lead or tungsten.

Waste Collecting Means

As shown in FIG. 2, the system 10 further comprises a waste collecting means in the form of a housing 620 and an evacuated vial 610 sealed with a septum 615, which is configured to be received within the housing 620 in use.

The housing 620 comprises a generally circular base portion 624 and a wall portion 623 extending upwardly from the base portion 624 and terminating at a top portion 622 to define a generally cylindrical shaped housing 620 with an internal volume 626.

The evacuated vial 610 can be sealed within the internal volume 626 of the housing 620 by virtue of a cap 625 that can be applied to the top portion 622 of the housing 620. The cap 625 comprises a generally circular top portion 627 and a skirt portion 628 disposed around the periphery of the top portion 627. The top portion 622 of the housing 620 has a slightly smaller external diameter than the base portion 624 and comprises an externally threaded portion (not shown). The skirt portion 628 of the cap 625 comprises a complementary internally threaded portion (not shown) to meshingly engage the externally threaded portion at the top portion 622 of the housing 620 to seal the vial 610 within the housing 620 in use.

The housing 620 and the cap 625 are both manufactured from a radiation shielding material such as lead or tungsten to shield users from exposure to any radioisotopes collected within the vial 610 if accidently eluted from the concentrator column 200. The external diameter of the evacuated vial 610 is smaller than, but complementary to, the internal diameter of the exit port 32e located at the top end portion 32a of the first body portion 32.

Process

Figure 5:
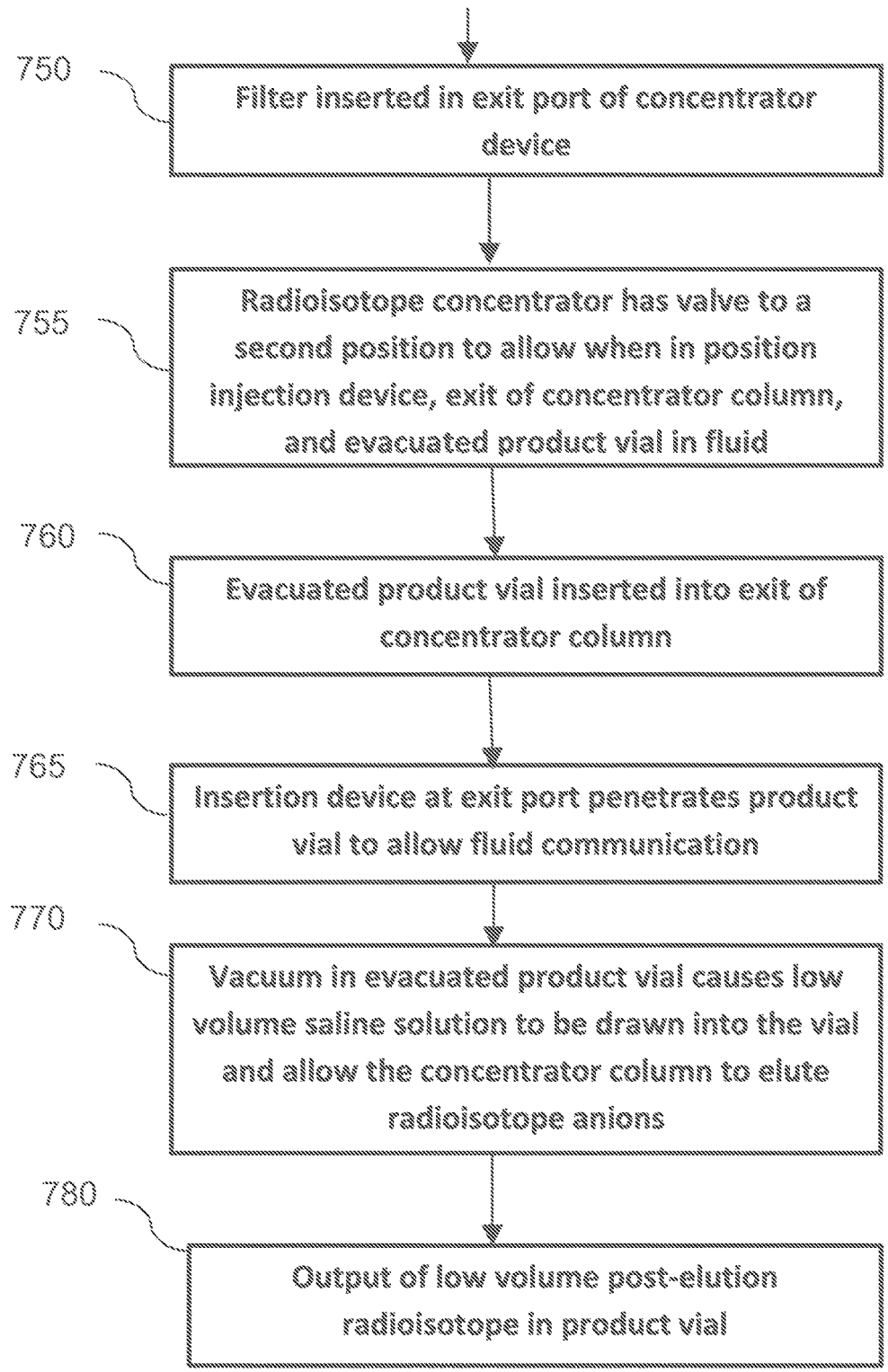
Figure 6:
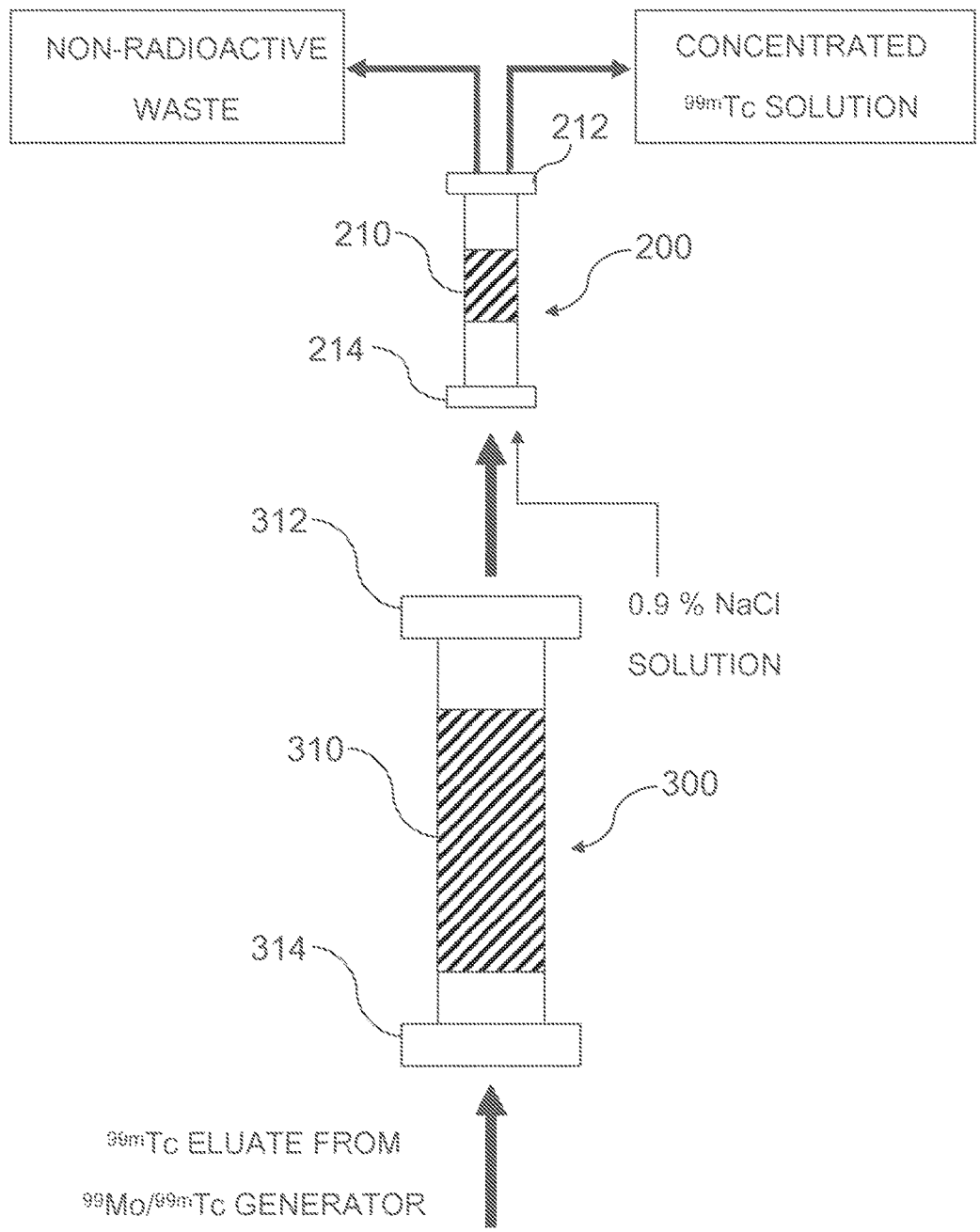
FIG. 6 shows a schematic representation illustrating a process for producing a concentrated radioisotope eluate solution in accordance with a preferred embodiment of the present disclosure.

Referring to FIGS. 5 and 6 there is shown a general process 700 using a radioisotope concentrator device 20 for selectively capturing radioisotopes from a highly dilute saline solution of radioisotopes eluted from the radioisotope generator 100 and then eluting the captured radioisotopes from the radioisotope concentrator device 20 as a pure and more concentrated saline solution of the desired radioisotopes by the radioisotope concentrator device 20 being configured for selectively capturing isotope from the saline solution eluted from the radioisotope generator 100 by the stationary phase packed within the column body 210 of the concentrator column 200 being either a multifunctional sorbent material or an inorganic sorbent selective to retard the radioisotope anions wherein the method includes the steps of:

the radioisotope concentrator having a valve, wherein with the valve is placed in a first position 710 such that the valve 400 is in the first open configuration and the HCISS column 300, the concentrator column 200, and the evacuated vial 610 being in fluid communication:

i. In a first step 715, the cylindrical entry port 34e of the assembled radioisotope concentrator device 20 and its self-aligning port is inserted into an elution port 110 of the radioisotope generator 100 at the bottom portion 314 of the HCISS column body 310.

ii. In a second step 720, the evacuated vial 610 of the waste collecting means is inverted and then inserted into the exit port 32e of the body 30 of the concentrator device 20 and the its self-aligning port enables fluid communication between the concentrator column 200 and the evacuated vial 610.

The a third step 735 has the vacuum within the evacuated vial 610 imparting a negative pressure on the system 10 causing the saline solution of radioisotope to be drawn up through the HCISS column 300 and the concentration column 200 into the vial 610.

In step 740 in this arrangement, the HCISS column 300 comprises a stationary phase that allows removing the competitive ions from the eluate solution and consecutively to allows selective capture (catching) of the desired radioisotope on either a multifunctional sorbent material or an inorganic sorbent in the concentrator column 200.

The remaining eluate solution is captured within the vial 610 as non-radioactive effluent waste in step 745.

The next step 750, the Millipore filter housed in a self-aligning insertion device is inserted into the exit port 32a of the body 30 of the concentrator device 20.

In a further step 755 has the radioisotope concentrator valve rotated to the second position such that the valve 400 is in the second open configuration and the injection device 45, the concentrator column 200, the Millipore filter 535, and the evacuated round bottom vial 510 of the pure and concentrated radioisotope solution collecting means 500 being in fluid communication wherein i. In step 760, the evacuated vial 510 of the radioisotope collecting means is placed within the housing 500 and sealed and the sealed housing 500 is then inverted and inserted into the exit port 32e of the body 30 of the radioisotope concentrator device 20;

ii. The insertion device at the exit port 32e penetrates the evacuated vial 510 in step 765 to enable fluid communication between the injection device 45, the concentrator column 200, and the evacuated vial 510;

iii. And in step 770 the vacuum within the evacuated vial 510 imparts a negative pressure on the system 10 causing the low volume saline solution to be drawn up from the injection device 45 into the vial 510 via the concentrator column 200 and allows the concentrator column 200 to elute (release) the selectively captured radioisotope anions from the concentrator column 200;

whereby the output 780 is the resulting low volume post-elution saline solution radioisotope in the vial 510 can be used for radio-labelling an organ-specific pharmaceutical or used directly without pharmaceutical tagging for specific procedures requiring only the radioisotope anions as the primary radiopharmaceutical.

FIG. 7 shows the effect of a general process 700 using the radioisotope concentrator device 20 for selectively capturing radioisotopes from a highly dilute saline solution of radioisotopes eluted from the radioisotope generator 100 and then eluting the captured radioisotopes from the radioisotope concentrator device 20 as a pure and more concentrated saline solution of the desired radioisotopes.

In this embodiment, the radioisotope generator 100 is a Mo-99/Tc-99m generator, and the radioisotope concentrator device 20 is configured for selectively capturing Technetium-99m (Tc-99m) from the saline solution of sodium pertechnetate $Na^+[^{99m}TcO_4^-]$ eluted from the Mo-99/Tc-99m generator 100. In this embodiment, the stationary phase (not shown) packed within the column body 210 of the concentrator column 200 is either a multifunctional sorbent material (a product of MEDISOTEC (Medical Isotope Techniques) as specified in Australia Patent Application AU2013903629 and published in WO/2015/039170, incorporated by reference herein) or an inorganic sorbent, which are selective to retarding the pertechnetate $[^{99m}TcO_4^-]$ anions.

The cylindrical entry port 34e of the assembled radioisotope concentrator device 20 is inserted into the elution port 110 of the Mo-99/Tc-99m generator 100 according to a first step, such that the hollow needle 120 of the Mo-99/Tc-99m generator 100 extends through the aperture 35 in the entry port 34e and at least the needle tip of the needle 120 penetrates the septum 325 at the bottom portion 314 of the HCISS column body 310.

The evacuated vial 610 of the waste collecting means is inverted and then inserted into the exit port 32e of the body 30 of the concentrator device 20 according to a second step. The needle tip of the needle 220 at the exit port 32e penetrates the septum 615 of the evacuated vial 610 to enable fluid communication between the concentrator column 200 and the evacuated vial 610.

In a third step, the lever 440 of the valve 400 is rotated to the second position such that the valve 400 is in the second open configuration and the HCISS column 300, the concentrator column 200, and the evacuated vial 610 are in fluid communication. The vacuum within the evacuated vial 610 imparts a negative pressure on the system 10 causing the saline solution of sodium pertechnetate $Na^+[^{99m}TcO_4^-]$ to be drawn up through the HCISS column 300 and the concentration column 200 into the vial 610. In this arrangement, the HCISS column 300 comprises a stationary phase (not shown) that is selective towards the chloride and Mo-99 anions of the saline eluate solution, while the pertechnetate $[^{99m}TcO_4^-]$ anions are selectively captured on the inorganic sorbent of the concentrator column 200. The remaining Tc-99m eluate solution is captured within the vial 610 as non-radioactive effluent waste. The vial 610 containing the non-radioactive effluent waste is then removed from the exit port 32e of the radioisotope concentrator device 20.

In a fourth step, the lever 440 of the valve 400 is rotated to the first position such that the valve 400 is in the first open configuration and the injection device 45, the concentrator column 200, and the evacuated vial 510 are in fluid communication.

In a fifth step, the evacuated vial 510 of the radioisotope collecting means is placed within the housing 500 and sealed using the cap 520. The sealed housing 500 is then inverted and inserted into the exit port 32e of the body 30 of the radioisotope concentrator device 20. The needle tip of the needle 220 at the exit port 32e penetrates the septum 515 of the evacuated vial 510 to enable fluid communication between the concentrator column 200, the sterile 0.22 µm-Millipore filter 535, and the evacuated vial 510.

The vacuum within the evacuated vial 510 imparts a negative pressure on the system 10 causing the low volume saline solution of pertechnetate $[^{99m}TcO_4^-]$ anions to be drawn up into the vial 510. A small volume of eluent, in this case, a normal saline [0.9%] solution, is then fluidly communicated from the injection device 45 to the concentrator column 200 to elute the selectively captured pertechnetate $[^{99m}TcO_4^-]$ anions from the concentrator column 200.

The resulting low volume post-elution saline solution of sodium pertechnetate in the vial 510 can be used for radiolabelling an organ-specific pharmaceutical or used directly without pharmaceutical tagging for specific procedures requiring only the $^{99m}TcO_4^-$ anions as the primary radiopharmaceutical.

In other embodiments, it will be appreciated by those skilled in the art that the desired radioisotopes for purification and concentration do not necessarily have to be first eluted from a radioisotope generator 100 before passing through the radioisotope concentrator device 20 as described above, but may simply be extracted from a solution of radioisotopes dissolved in a vial (not shown) that is introduced at the cylindrical entry port 34e of the assembled radioisotope concentrator device 20 and then drawn up through the columns within the radioisotope concentrator device 20 by virtue of the vacuum afforded by the evacuated vials 610 and 510 at the relevant stage of the purification and concentration process, respectively. In one arrangement, it will be appreciated by those skilled in the art that the vial comprising the radioisotope solution is capped with a septum. As such, the vial is inserted into the cylindrical entry port 34e of the assembled radioisotope concentrator device 20, and a double-ended hollow needle (not shown) is employed to operably connect the vial to the radioisotope concentrator device 20 by virtue of a needle tip at one end of the hollow needle penetrating the septum in the vial and a needle tip at the other end of the hollow needle extending through the aperture 35 in the entry port 34e and penetrating the septum 325 at the bottom portion 314 of the HCISS column body 310 to enable fluid communication of the radioisotope solution from the vial to the radioisotope concentrator device 20.

EXAMPLES

The following examples are put forth so as to provide persons skilled in the art with a complete disclosure and description of how to use the radioisotope concentrator device 20 according to the preferred embodiments of the present disclosure, and is not intended to limit the scope of the present disclosure.

Every effort has been made to ensure accuracy with respect to numbers (e.g., concentration factors, radioactivity, life time, etc.) but some errors and deviations should be accounted for. Unless indicated otherwise, radioactivity is in mCi/GBq, where [1 curie (Ci) is 37 Giga Becquerels (GBq) and 1 Bq is $2.7027 \times 10^{-11}$ Ci], the concentration factor is measured by [Radioisotope concentration in solution volume (before)]/ [Radioisotope concentration in solution volume (after)] (no units), and the life time is measured in days.

Example 1

A study was performed using the radioisotope concentrator device 20 described in the embodiments above mounted to the elution port 110 of a Mo-99/Tc-99m generator 100. The volume of the Tc-99m eluate solution generated from the Mo-99/Tc-99m generator was 10 mL. After passing the Tc-99m solution through the radioisotope concentrator device 20 (a process time of less than 5 minutes), the selectively captured pertechnetate anions were eluted with 0.9% saline solution to achieve a post-elution Tc-99m solution with a volume of 1.0 mL, corresponding to a concentration factor of 10.

In other examples, concentration factors of between 10 and 20 have been achieved.

Example 2

A study was conducted using two commercially available radioisotope generators to evaluate the effectiveness of the post-elution Tc-99m concentrating process for increasing the useful life time of the Mo-99/Tc-99m generator.

The results of the study are listed in Table 1.

TABLE 1

| Radio-activity of generator (mCi/GBq) | Life time of generator useful for clinical SPECT imaging (Days) | | Life time of generator useful for the Cyclomedia Technegas Plus System (Days) | |
|---|---|---|---|---|
| | Without Tc-99m concentration | With post-elution concentration of Tc-99m | Without Tc-99m concentration | With post-elution concentration of Tc-99m |
| 100/3.7 | 1 | 6 | 0 | 1 |
| 300/11.1 | 4 | 10 | 0 | 4 |
| 500/18.5 | 6 | 12 | 0 | 6 |
| 1000/37.0 | 9 | 15 | 1 | 9 |
| 3000/111.0 | 14 | 20 | 4 | 14 |

Example 3

A study was performed using a vial (not shown) comprising 20 mL of a Tc-99m radioisotope solution housed in a radioactive shielded body (not shown) which was inserted into the cylindrical entry port 34e of the assembled radioisotope concentrator device 20, and operably connected to the HCISS column body 310 by virtue of a double-ended hollow needle (not shown). The Tc-99m radioisotope solution was drawn through the radioisotope concentrator device 20 under vacuum and flushed with 5 mL of distilled water (process time of less than 10 minutes). The pertechnetate [$^{99m}TcO_4^-$] anions selectively captured on the concentrator column 200 were eluted with 0.9% saline solution to achieve a post-elution Tc-99m radioisotope solution with a volume of 1.0 mL, corresponding to a concentration factor of 20.

In other examples, concentration factors of between 10 and 50 have been achieved.

Advantages

The ability to selectively capture and extract radioisotopes on a small concentrator column 200 loaded with less than 50 mg of either multifunctional sorbent material as specified in Australia Patent Application AU2013903629 (and published in WO/2015/039170) or inorganic sorbent, and re-solubilize them in a very small volume of saline solution enables a post-elution radioisotope eluate solution to be produced that has a higher radioisotope concentration than the radioisotope solution eluted from the radioisotope generator 100. The HCISS column 300 assures the efficiency of a small size (typically 50 mg of either multifunctional sorbent material as specified in Australia Patent Application AU2013903629 (WO/2015/039170) or inorganic sorbent) concentrator column 200 over multiple concentration cycles. The small size of the concentrator column 200 is essential to minimize the volume of the desired radioisotope solution in the final concentration step and increases the resulting concentration factor.

The use of evacuated vials 510 and 610, and thus the resulting negative pressure imparted on the system 10 to drive the process 700, provides a simple and effective means of producing post-elution radioisotope eluate solutions without resorting to the use of pump(s).

The use of sterile components (namely, the concentrator column 200, the HCISS column 300, the valve 400, and the 0.22 micron in-line filters) ensures that the process 700 can be performed repeatedly under sterile filtration conditions.

The sterile components (namely, the valve 400, the injection device, the concentrator column 200 and the HCISS column 300) used in radioisotope concentrator device 20 are commercially available consumable products.

In other embodiments, the radioisotope concentrator device 20 may be configured for use with a radioisotope generator 100 that is configured for generating Re-188 radioisotopes. It will be appreciated that the choice of stationary phase within the concentrator column 200 will be selected according to the type of radioisotope generated.

In other embodiments, the radioisotope concentrator device 20 may be configured for use with a double-ended hollow needle device (not shown) that is configured for operably connecting a radioisotope solution source (not shown) thereto. In this arrangement, the radioisotope solutions/eluates generated from several radioisotope generators (not shown) could be combined together and concentrated using the radioisotope concentrator device 20 in one step.

In other embodiments, the volume of 0.9% normal saline solution used to elute the radioisotopes from the concentrator column 200 may be in the range from approximately 0.1 mL to approximately 2.0 mL.

Interpretation

Embodiments

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Terminology

In describing the preferred embodiment of the disclosure illustrated in the drawings, specific terminology will be resorted to for the sake of clarity. However, the disclosure is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the disclosure.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the medical diagnostic industry.

The claims defining the invention are as follows:

1. A radioisotope concentrator device for use with a radioisotope source, the radioisotope concentrator device comprising:
 a body having an internal volume in the form of a multiple use sterile disposable cartridge including a concentrator column, a competitive ion selective column, an injection device comprising at least one injection port, one multiple way valve, one entry port at a lower location, and one exit port at an upper location, all being in fluid communication;
 the concentrator column disposed within the internal volume being adapted for selectively capturing at least one radioisotope from a radioisotope solution obtained from a radioisotope source in use, and the body having shielding means for shielding at least the concentrator column in use;
 the competitive ion selective column disposed within the internal volume being adapted for removing at least one competitive ion from the radioisotope solution obtained from the radioisotope source in use;
 the at least one injection port adapted to receive an injection device, and the at least one injection port being operably connected to the concentrator column;
 the one multiple way valve being configurable between a first open configuration for allowing fluid communication between the competitive ion selective column and the concentrator column in use and a second open configuration for allowing fluid communication between the at least one injection port and the concentrator column to elute the at least one radioisotope from the concentrator column with an eluent; and
 wherein the at least one exit port, being in fluid communication with the internal volume and the at least one exit port, is able to connect to an evacuated vial in use to effect, by the vacuum provided by the waste vial, the fluid communication in the first open configuration or in the second open configuration and whereby the vacuum within the evacuated vial imparts a negative pressure on the system causing the solution of the radioisotope with the eluent to be drawn up through the competitive ion selective column and the concentrator column into the vial.

2. A radioisotope concentrator device as claimed in claim 1 wherein the fluid communication in one configurable way is between one competitive ion selective sorbent column, the concentrator column, an injection device, a Millipore filter, and the radioisotope source in use, which fluid communication is effected by the vacuum, wherein the vacuum is provided by the waste vial being connected to the exit of the concentrator device and the vacuum from the evacuated waste vial causing saline solution of radioisotope to be drawn into a Halide and Competitive Ion Selective Sorbent (HCISS) column, the concentration column, and the waste vial.

3. A radioisotope concentrator device as claimed in claim 1 wherein radioisotope source is selected from Molybdenum/Technetium pairs for the separation/purification of Technetium from Molybdenum or Tungsten/Rhenium for the separation/purification is of Rhenium from Tungsten.

4. A radioisotope concentrator device as claimed in claim 2 wherein the body further comprises at least one exit port, the concentrator column being in fluid communication with the at least one exit port wherein the at least one exit port comprises connecting means for connecting to an evacuated vial in use and wherein the connecting means comprises a needle device to at least partially penetrate a septum of the evacuated vial in use.

5. A radioisotope concentrator device as claimed in claim 1 wherein the radioisotope source is a radioisotope generator configured for generating the radioisotope solution, and wherein the radioisotope generator comprises an elution port, the radioisotope concentrator device further comprising a body having at least one entry port adapted for connecting to the elution port of the radioisotope generator in use.

6. A radioisotope concentrator device as claimed in claim 5 wherein the elution port of the radioisotope generator comprises a needle device, the at least one entry port of the body of the radioisotope concentrator device comprising a septum adapted to receive at least a portion of the needle device therethrough when connecting the radioisotope concentrator device to the elution port of the radioisotope generator in use.

7. A radioisotope concentrator device as claimed in claim 1 wherein the radioisotope source is a vial comprising the radioisotope solution wherein the vial comprises a septum, the radioisotope concentrator device further comprising a body having at least one entry port equipped with a septum, each septum being adapted to receive at least a portion of a corresponding end of a double-ended hollow needle device when connecting the vial to the radioisotope concentrator device in use.

8. A radioisotope concentrator device as claimed in claim 1 wherein the body is generally elongate having a bottom portion, a top portion, and a wall portion extending between the bottom portion and the top portion, each of the bottom portion, the top portion, and the wall portion being manufactured from a radiation shielding material, wherein the radiation shielding material is lead or tungsten.

9. A radioisotope concentrator device as claimed in claim 1, further comprising a competitive ion selective column adapted for removing at least one competitive ion from the radioisotope solution obtained from the radioisotope source in use, wherein the competitive ion selective column comprises a sorbent means for selectively capturing the at least one competitive ion in use, and wherein the competitive ion selective column is located upstream of the concentrator column and is in fluid communication with the concentrator column.

10. A radioisotope concentrator device as claimed in claim 9, further comprising a body having an internal volume, the competitive ion selective column being located substantially within the internal volume of the body in use, wherein the body comprises support means for supporting the competitive ion selective column substantially within the internal volume of the body in use.

11. A radioisotope concentrator device as claimed in claim 9, wherein the at least one competitive ion is selected from the group of competitive ions comprising a halide anion and a breakthrough impurity ion.

12. A radioisotope concentrator device as claimed in claim 11 wherein the halide anion is a chloride anion.

13. A radioisotope concentrator device as claimed in claim 11 wherein the radioisotope source is a $^{99}$Mo/$^{99m}$Tc radioisotope generator, the radioisotope solution obtained from the $^{99}$Mo/$^{99m}$Tc radioisotope generator comprising a $^{99}$Mo breakthrough impurity ion.

14. A radioisotope concentrator device as claimed in claim 11 wherein the radioisotope source is a $^{188}$W/$^{188}$Re radioisotope generator, and the radioisotope solution is obtained from the $^{188}$W/$^{188}$Re radioisotope generator comprising a $^{188}$W breakthrough impurity ion.

15. A radioisotope concentrator device as claimed in claim 1 wherein the body comprises at least one injection port adapted to receive an injection device, the at least one injection port being operably connected to the concentrator column and further comprising at least one valve being configurable between a first open configuration for allowing fluid communication between the competitive ion selective column and the concentrator column in use and a second open configuration for allowing fluid communication between the at least one injection port and the concentrator column to elute the at least one radioisotope from the concentrator column with an eluent, wherein the body further comprises at least one exit port, the at least one valve being adapted for enabling fluid communication between the at least one injection port and the at least one exit port when the at least one valve is in the second open configuration, wherein the body further comprises at least one entry port and at least one exit port, the at least one valve being adapted for enabling fluid communication between the at least one entry port and the at least one exit port when the at least one valve is in the first open configuration.

16. A radioisotope concentrator device as claimed in claim 15 wherein the single unit composed of the concentrator column, competitive ion selective column, valve, and injection device is a sterile disposable cartridge, the housing composed of the cylindrical portions is for multiple uses and for each use, one disposable cartridge (single unit) is inserted into the housing and a sterile disposable cartridge is used for multiple concentration procedures.

17. A radioisotope concentrator device as claimed in claim 1 wherein the radioisotope source is a vial comprising the radioisotope solution.

18. A radioisotope concentrator device as claimed in claim 17 wherein the vial comprises a septum, the body further comprising at least one entry port equipped with a septum, the at least one entry port being in fluid communication with the internal volume, each septum being adapted to receive at least a portion of a corresponding end of a double-ended hollow needle device when connecting the vial to the radioisotope concentrator device in use.

* * * * *